US006548171B1

United States Patent
Barbera-Guillem et al.

(10) Patent No.: US 6,548,171 B1
(45) Date of Patent: Apr. 15, 2003

(54) FLUORESCENT NANOCRYSTAL-EMBEDDED MICROSPHERES FOR FLUORESCENCE ANALYSES

(76) Inventors: Emilio Barbera-Guillem, 1555 Picarde Ct., Powell, OH (US) 43065; Stephanie L. Castro, 6167 Millbourne Dr., Columbus, OH (US) 43230

(*) Notice: Subject to any disclaimer, the term of this patent is extended or adjusted under 35 U.S.C. 154(b) by 161 days.

(21) Appl. No.: 09/633,953

(22) Filed: Aug. 8, 2000

Related U.S. Application Data

(63) Continuation-in-part of application No. 09/436,145, filed on Nov. 9, 1999.
(60) Provisional application No. 60/107,829, filed on Nov. 10, 1998.

(51) Int. Cl.$^7$ ............................................. B32B 15/02
(52) U.S. Cl. .................. 428/402.24; 428/402; 428/403; 428/404; 428/407; 436/523; 436/533; 523/200; 523/201
(58) Field of Search ........................ 428/402, 402.24, 428/403, 404, 407; 436/523, 533; 523/200, 201; 424/9.36, 9.6

(56) References Cited

U.S. PATENT DOCUMENTS

| | | |
|---|---|---|
| 4,767,205 A | 8/1988 | Schwartz et al. |
| 5,194,300 A | 3/1993 | Cheung |
| 5,289,547 A | 2/1994 | Ligas |
| 5,592,561 A | 1/1997 | Moore et al. |
| 5,747,349 A | 5/1998 | van den Engh et al. |
| 5,786,219 A | 7/1998 | Zhang et al. ............... 436/523 |
| 5,990,479 A | 11/1999 | Weiss et al. ................ 250/307 |
| 6,114,038 A | 9/2000 | Castro et al. |
| 6,309,701 B1 | 10/2001 | Bargera-Guillem |

OTHER PUBLICATIONS

Emory et al.; Direct Observation of Size–Dependent Optical Enhancement in Single Metal Nanoparticles. J. Am. Chem. Soc. 1998, 120, 8009–8010.
Kaiser; Raising the Stakes in the Race for New Malaria Drugs, Science, vol. 281, p. 1930–1931; Sep. 25, 1998.
Jacoby, Quantum Dots Meet Biomolecules; C & EN, p. 8; Sep. 28, 1998.
Bruchez Jr. et al., Semiconductor nanocrystals as fluorescent biological labels, Sep. 1998, Science, 281:2013–2015.
Chan et al., Quantum dot bioconjugates for ultrasensitive nonisoptopisc detection, Sep. 1998, Science, 281:2016–2018.
Castro, BioPixel nanocrystalline fluorescent markers, Oct. 1999, Genetic Engineering News, vol. 19, No. 17.

*Primary Examiner*—Samuel A. Acquah
(74) *Attorney, Agent, or Firm*—Raymond A. Miller; Pepper Hamilton LLP

(57) ABSTRACT

Provided are a fluorescent microsphere comprised of a plurality of fluorescent nanocrystals embedded in a polymeric microsphere; a kit prepared from the fluorescent microspheres; and a method of producing the fluorescent microspheres comprising swelling the polymeric microsphere so that into its pores can enter fluorescent nanocrystals, and then unswelling the polymeric micropsheres so that the fluorescent nanocrystals become physically entrapped in the pores of the unswelled polymeric microsphere. Also provided is a method of using the fluorescent microspheres comprising affinity ligand for determining the presence or absence of a predetermined number of analytes in a sample by contacting the sample with the fluorescent microspheres, and detecting the fluorescence signal pattern of excited fluorescent microspheres bound to one or more analytes of the predetermined number of analytes, if present in the sample.

40 Claims, 1 Drawing Sheet

FLUORESCENT NANOCRYSTAL-EMBEDDED MICROSPHERES FOR FLUORESCENCE ANALYSES

This is a continuation-in-part application based on co-pending U.S. Ser. No. 09/436,145 filed Nov. 9, 1999 which is a nonprovisional application based on U.S. Ser. No. 60/107,829 filed Nov. 10, 1998, the disclosures of which are herein incorporated by reference.

FIELD OF THE INVENTION

This invention relates to polymer-based microspheres, wherein the microspheres are labeled with one or more types of fluorescent nanocrystals. The resulting fluorescent microspheres are useful as distinct tagging agents or as encoders in methods utilizing fluorescence-based detection such as microarrays, high-throughput screening, immunoassays, and flow cytometry.

BACKGROUND OF THE INVENTION

Fluorescent polymeric microspheres have been described as comprising either microspheres which are surface-labeled (including surface-coated) with fluorescent dyes, or microspheres having structurally incorporated within their volume (e.g., embedded or polymerized therein) a fluorescent dye. Commonly used fluorescence-based analyses that utilize fluorescent microspheres generally apply the microspheres for a purpose selected from the group consisting of: as a detection reagent with an affinity ligand bound thereto in assaying for the presence of a molecule for which the affinity ligand has binding specificity, as a calibrating agent for calibrating fluorescence-based detection systems, as a tracer (e.g., to trace the flow of a fluid containing the microspheres), and a combination thereof.

Typically, conventional fluorescent dyes (e.g., fluorescein, rhodamine, phycoerythrin, and the like) are used for labeling microspheres. These conventional fluorescent dyes typically have an excitation spectrum that may be quite narrow; hence, it is often difficult to find a wavelength spectrum of light suitable for simultaneously exciting several different fluorescent labels (e.g., differing in color of fluorescence emission). However, even when a single light source is used-to provide a excitation wavelength spectrum (in view of the spectral line width), often there is insufficient spectral spacing between the emission optima of different species (e.g., differing in color) of fluorescent dyes to permit individual and quantitative detection without substantial spectral overlap. Additionally, conventional fluorescent dyes are susceptible to photobleaching which limits the time in which a fluorescent signal can be detected, and limits time-resolved fluorescence (fluorescent signal integration over time). Additional limitations of fluorescent dyes include fluorescence quenching, and shifts in fluorescence emission spectra, depending on the environment in which dyes are excited.

Fluorescent nanocrystals comprising either semiconductor nanocrystals or doped metal oxide nanocrystals have been reported to resist photobleaching, share an excitation wavelength spectrum, and are capable of emitting fluorescence of high quantum yield and with discrete peak emission spectra. However, these nanocrystals lack sufficient solubility in aqueous-based environments required for labeling microspheres; i.e., in aqueous-based environments, the nanocrystals interact together in forming aggregates, which leads to irreversible flocculation of the nanocrystals.

Thus, there remains a need for fluorescent microspheres that: (a) maybe used in either single color or multicolor analysis; (b) are comprised of fluorescent nanocrystals which are sufficiently soluble in aqueous-based solutions to permit an effective concentration of the fluorescent nanocrystals to be embedded into polymeric microspheres in forming fluorescent microspheres; (c) which may be excited with a single wavelength spectrum of light resulting in detectable fluorescence of high quantum yield and with discrete peak emission spectra; (d) that are not susceptible to photobleaching and (e) which may further comprise one or more molecules of affinity ligand for use in fluorescence-based detection systems.

SUMMARY OF THE INVENTION

Provided is a fluorescent microsphere comprised of a polymeric microsphere that has embedded in its surface a plurality of at least one type of fluorescent nanocrystals, such that following excitation of the fluorescent microsphere with an appropriate excitation wavelength spectrum, the fluorescent microsphere will emit fluorescence of high quantum yield and with discrete peak emission. Fluorescent microspheres may differ in size and composition, and can be varied in the intensity of fluorescence emission and the one or more colors of fluorescence emission by changing the amount and type of fluorescent nanocrystals, respectively, in the method of preparing the microspheres. Thus, the fluorescent properties of the fluorescent microspheres, such as intensity and color, are sensitive to the corresponding fluorescent nanocrystals used to produce the fluorescent microspheres. A resultant advantage of the fluorescent microspheres of the present invention is that they may be used for measuring a plurality of analytes in a single sample. For example, a first population of fluorescent microspheres (a) may have embedded in their respective surface a plurality of one type of fluorescent nanocrystals which will emit a red fluorescent signal upon excitation, and (b) be tagged with affinity ligand having binding specificity for a first analyte. A second population of fluorescent microspheres (a) may have embedded in their respective surface a plurality of one type of fluorescent nanocrystals which will emit a yellow fluorescent signal upon excitation, and (b) be tagged with affinity ligand having binding specificity for a second analyte. Thus, because the first and second populations of fluorescent microspheres can be excited with a single wavelength spectrum of light resulting in detectable fluorescence of high quantum yield and with discrete peak emission spectra, and because the first and second populations of fluorescent microspheres can bind their respective analyte (via their affinity ligand), the two populations of fluorescent microspheres can be mixed within one sample in simultaneously measuring for the presence of the first and second analytes..

Advantages of the fluorescent microspheres over individual nanocrystals which have been functionalized to include an affinity ligand, include the following. First, a single nanocrystal may only be functionalized with a limited number of affinity ligands. In contrast, a fluorescent microsphere according to the present invention can have embedded in its surface a far greater number of fluorescent nanocrystals in enabling a fluorescent signal much greater in intensity than a single fluorescent nanocrystal can emit. Such an advantage is particularly useful in measuring an analyte which is present in minute quantities (and hence, can be bound by only a limited number of affinity ligand). Additionally, more than one type of fluorescent nanocrystal may be used for embedding into the surface of a fluorescent microsphere. Hence, the fluorescent microsphere may comprise a plurality of types of fluorescent nanocrystals embedded in its surface in encoding the fluorescent microsphere with a specific, identifiable code (based on the emission spectra which can comprise both color and intensity) which can be used to distinguish a population of these microspheres from a population of fluorescent microspheres which are encoded with a different fluorescence pattern. Such encoded fluorescent microspheres are particularly suited for multi-dimensional microarray formats. Further, in a method of producing the fluorescent microspheres according to the present invention, by controlling the proportion of starting materials (e.g., number of polymeric microspheres, and the number and composition of fluorescent nanocrystals), precise control may be achieved with respect to the basic fluorescent properties of the resultant fluorescent microspheres. Also provided is a kit comprising the fluorescent microspheres, and may further comprise the fluorescent microspheres operably bound to affinity ligand.

The above and other objects, features, and advantages of the present invention will be apparent in the following Detailed Description of the Invention when read in conjunction with the accompanying drawings.

DETAILED DESCRIPTION OF THE INVENTION

Definitions

Figure 1:
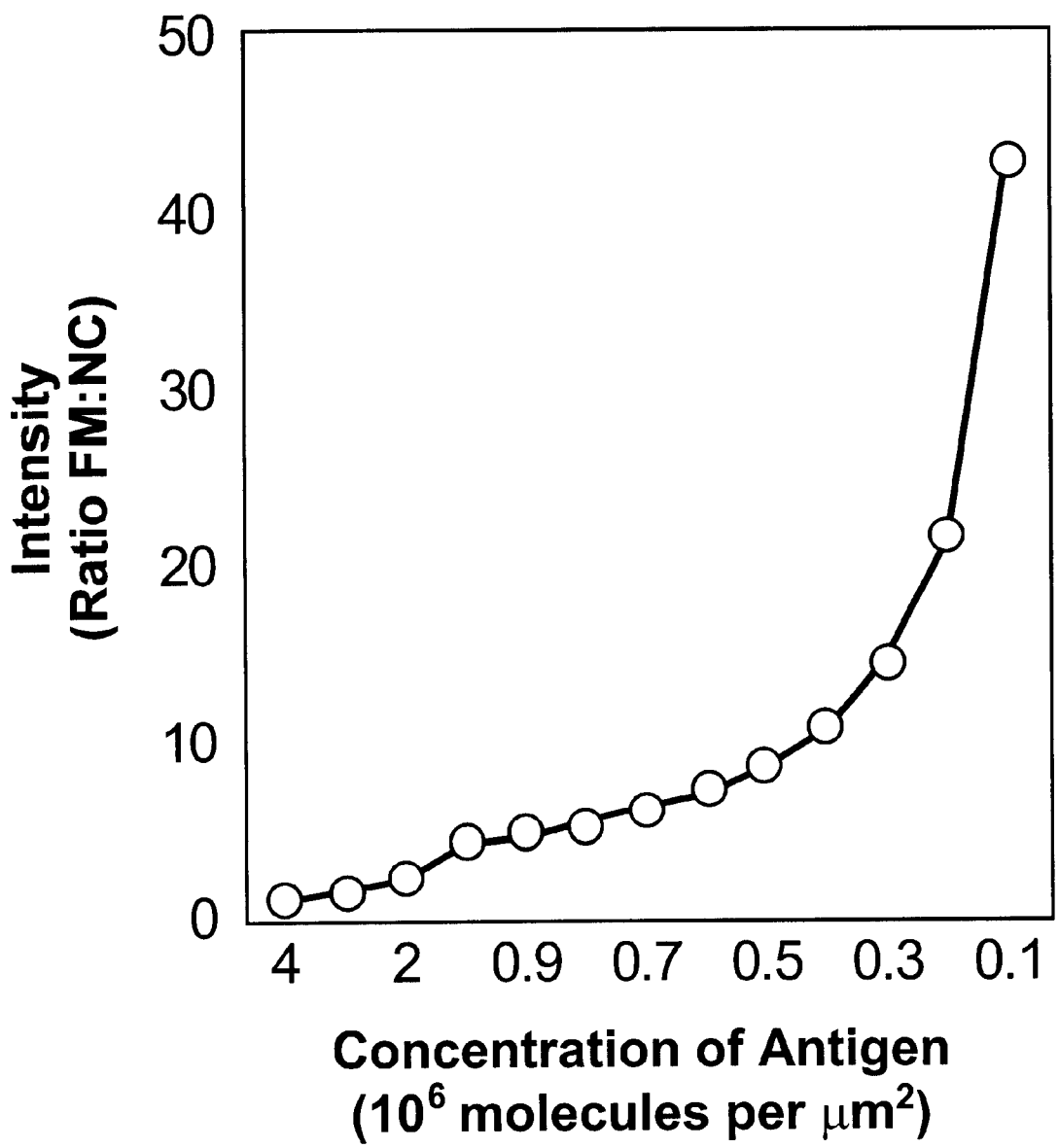
FIG. 1 is a graph illustrating the relative intensity of an exemplary fluorescent microsphere according to the present invention, as compared to that of a fluorescent nanocrystal.

By the term "analyte" is meant, for the purposes of the specification and claims to refer to a molecule of an organic or inorganic nature, the presence and/or quantity of which is being tested for; and which contains a molecular component (domain or sequence or epitope or portion or chemical group or determinant) for which the affinity ligand has binding specificity. The molecule may include, but is not limited to, a nucleic acid molecule protein, glyco-protein, eukaryotic or prokaryotic cell, lipoprotein, peptide, carbohydrate, lipid, phospholipld, aminoglycans, chemical messenger, biological receptor, structural component, metabolic product, enzyme, antigen, drug, therapeutic, toxin, inorganic chemical, organic chemical, and the like.

By the term "affinity ligand" is meant, for purposes of the specification and claims, to mean a molecule which has binding specificity and avidity for a molecular component of, or associated with, an analyte. In general, affinity ligands are known to those skilled in the art to include, but are.not limited to, lectins or fragments (or derivatives) thereof which retain binding function; monoclonal antibodies ("mAb", including chimeric or genetically modified monoclonal antibodies (e.g., "humanized")); peptides; aptamers; nucleic acid molecules (including, but not limited to, single stranded RNA or single-stranded DNA, or single-stranded nucleic acid hybrids); avidin, or streptavidin, or avidin derivatives; and the like. The invention may be practiced using a preferred affinity ligand (e.g., a mAb) to the exclusion of affinity ligands other than the preferred affinity ligand. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include $F(ab+)_2$ Fab', Fab, Fv, scFV, Fd' and Fd fragments. Methods for producing the various fragments or derivatives from mAbs are well known in the art (see, e.g., Plückthum, 1992, Immunol. Rev. 130:152–188). For example, $F(ab')_2$ can be produced by pepsin digestion of the monoclonal antibody, and Fab' may be produced by reducing the disulfide bridges of $F(ab')_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. Aptamers can be made using methods described in U.S. Pat. No. 5,789,157 (herein incorporated by reference). Lectins, and fragments thereof, are commercially available.

By the term "fluorescent microsphere" is meant, for purposes of the specification and claims to refer to a polymeric microsphere having embedded in its surface a plurality of fluorescent nanocrystals, as will be more apparent from the following descriptions.

By the term "polymeric microsphere" is meant, for purposes of the specification and claims to refer to a bead which is substantially spherical in shape, and is comprised of a polymeric material which may include, but is not limited to, latex, acrylic, glass/polymer composites (see, e.g., U.S. Pat. No. 5,507,990), a thermoplastic (e.g., one or more of polystyrenes, polyvinyl chloride, polyacrylate, nylon, substituted styrenes, polyamides, polycarbonate, polymethylacrylic acids, polyaldehydes, and the like), a magnetic material in combination with a polymeric material, and a combination thereof. For purposes of the invention, such a polymeric microsphere excludes the inclusion of a blowing agent therein (i.e., does not contain a cavity containing a volatile liquid). In one embodiment, the polymeric material may further comprise carbon black in a % weight in a range of from about 0.5 to about 5 with respect to the polymeric material, which may minimize (reduce or quench) intrinsic fluorescence of the polymeric material, if any. For example, the carbon black may be mixed into a solution of a thermoplastic, and then the mixture is plasticized into a solid composite. In a preferred embodiment, the polymeric microspheres may further comprise-one or more molecules of affinity ligand operably bound thereto. Methods for operably binding affinity ligand to the surface of polymeric microspheres are well known in the art. Depending on the composition of the polymeric microspheres, typically the microspheres will comprise one or more types of reactive functionalities which react with reactive functionalities of an affinity ligand resulting in affinity ligand being operably bound to the polymeric microspheres. In a preferred embodiment, the one or more types of reactive functionalities present on the surface of the polymeric microsphere comprises a plurality of carboxyl-reactive groups, a plurality of amine-reactive groups, or a combination thereof. In a preferred embodiment, the average diameter of the polymeric sphere is in a range of from about 0.05 micron ($\mu$m) to about 500 $\mu$m; and most preferably, in a range of from about 0.1 $\mu$m to about 10 $\mu$m. As will be appreciated by those skilled in the art, the composition, shape, size, and density of the polymeric microsphere may vary depending on the factors such as the assay system in which it is used, as well as the nature of an analyte to be detected. A preferred polymeric microsphere may be used to the exclusion of a polymeric microsphere other than the preferred polymeric microsphere.

By the term "fluorescent nanocrystals" is meant, for purposes of the specification and claims to refer to nanocrystals comprising semiconductor nanocrystals or doped metal oxide nanocrystals, wherein the nanocrystals are operably bound to, and functionalized by the addition of, a plurality of molecules which provide the functionalized fluorescent nanocrystals with reactive functionalities; and wherein the preferred plurality of molecules is selected from the group consisting of carboxylic acid, diaminocarboxylic acid, a monoaminocarboxylic acid, and a combination thereof. A preferred type of molecules may be used to the exclusion of molecules other than the preferred type of molecules. In a preferred embodiment, the functionalized nanocrystals are sufficiently soluble in an aqueous-based environment to permit the fluorescent nanocrystals to be embedded in the polymeric microspheres in forming fluorescent microspheres in an aqueous-based environment.

By the term "semiconductor nanocrystals" is meant, for purposes of the specification and claims to refer to quantum dots (crystalline semiconductors) comprised of a core comprised of at least one of a Group II-VI semiconductor material (of which ZnS, and CdSe are illustrative examples), or a Group III-V semiconductor material (of which GaAs is an illustrative example), a Group IV semiconductor material, or a combination thereof. In a preferred embodiment, the core of the quantum dots may be passivated with an semiconductor overlayering ("shell") uniformly deposited thereon. For example, a Group II-VI semiconductor core may be passivated with a Group II-VI semiconductor shell (e.g., a ZnS or CdSe core may be passivated with a shell comprised of YZ wherein Y is Cd or Zn, and Z is S, or Se). As known to those skilled in the art, the size of the semiconductor core correlates with the spectral range of emission. Table 1 is an illustrative example for CdSe.

TABLE 1

| Color | Size Range (nm) | Peak Emission Range |
|-------|-----------------|---------------------|
| blue | 2.5 to 2.68 | 476 to 486 |
| green | 2.8 to 3.4 | 500 to 530 |
| yellow | 3.58 to 4.26 | 536 to 564 |
| orange | 4.9 to 6.1 | 590 to 620 |
| red | 8.6 to 10.2 | 644 to 654 |

In a preferred embodiment, the semiconductor nanocrystals are produced using a continuous flow process and system disclosed in copending U.S. application Ser. No. 09/468,418 (the disclosure of which is herein incorporated by reference), and have a particle size that varies by less than +/−4% in the average particle size. In a preferred embodiment, the semiconductor nanocrystals comprise a monodisperse population having an average particle size (as measure by diameter) in the range of approximately 1 nanometer (nm) to approximately 20 nm.

By the term "doped metal oxide nanocrystals" is meant, for purposes of the specification and claims to refer to nanocrystals comprised of: a metal oxide, and a dopant comprised of one or more rare earth elements. For example, suitable metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. The rare earth element comprises an element selected from the Lanthanide series and includes, but is not limited to, europium (Eu), cerium (Ce), neodymium (Nd), samarium (Sm), terbium (Tb), gadolinium (Gd), holmium (Ho), thulium (Tm), an oxide thereof, and a combination thereof. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used to label a microsphere according to the present invention. A given rare earth or rare earth combination has a given color, thereby permitting the provision of doped metal oxide nanocrystals, each of which may emit (with a narrow emission peak) a color over an entire range of colors by adjusting the nature of the dopant, the concentration of the dopant, or a combination thereof. For example, the emission color and brightness (e.g., intensity) of a doped metal oxide nanocrystal comprising $Y_2O_3$:Eu may depend on the concentration of Eu; e.g., emission color may shift from yellow to red with increasing Eu concentration. For purposes of illustration only, representative colors which may be provided are listed in Table 2.

TABLE 2

| Fluorescent Color | Dopant |
|-------------------|--------|
| blue | thulium |
| blue | cerium |
| yellow-green | terbium |
| green | holmium |
| green | erbium |
| red | europium |
| reddish orange | samarium |
| orange | neodymium |
| yellow | dysprosium |
| white | praseodymium |
| orange-yellow | europium + terbium |
| orange-red | europium + samarium |

Methods for making doped metal oxide nanocrystals are known to include, but are not limited to a sol-gel process (see, e.g., U.S. Pat. No. 5,637,258), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm. In a preferred embodiment, the doped metal oxide nanocrystals are comprised of metal oxides doped with one or more rare earth elements, wherein the dopant comprising the rare earth element is capable of being excited (e.g., with ultraviolet light) to produce a narrow spectrum of fluorescence emission. In another preferred embodiment, the doped metal oxide has both fluorescent properties (when excited with an excitation light source) and magnetic properties; thus, a polymeric microsphere (which is substantially nonmagnetic) embedded with a plurality of fluorescent nanocrystals (comprising doped metal oxide nanocrystals which are magnetic material) may form fluorescent microspheres according to the present invention which are magnetic.

By the term "operably bound" is meant, for purposes of the specification and claims to refer to fusion or bond or an association of sufficient stability to withstand conditions encountered in a method of detection, between a combination of different molecules such as, but not limited to, between a fluorescent nanocrystal and the molecules by which they are functionalized (e.g., carboxylic acid, diaminocarboxylic acid, or a monoaminocarboxylic acid), a fluorescent microsphere and affinity ligand, and a combination thereof. As known to those skilled in the art, the bond may comprise one or more of covalent, ionic, hydrogen, van der Waals, and the like. As known to those skilled in the art, and as will be more apparent by the following embodiments; there are several methods and compositions in which two or more molecules may be operably bound utilizing reactive functionalities. Reactive functionalities include, but are not limited to, free chemical groups (e.g., thiol, or carboxyl, hydroxyl, amino, amine, sulfo, etc.), and reactive chemical groups (reactive with free chemical groups).

The term "suitable conditions" is used herein, for purposes of the specification and claims, and with reference to a process of reacting two components (e.g., polymeric microsphere and fluorescent nanocrystals; fluorescent microsphere comprising affinity ligand and an analyte for which the affinity ligand has binding specificity), to mean those conditions under which the components may become bound to each other. For example, "suitable conditions" for reacting an analyte with an affinity ligand (such as a fluorescent microsphere comprising affinity ligand) so that the components become operably bound are known to those skilled in the art to include one or more of: a pH range of from about 3 to about 9, ionic strengths such as that ranging from distilled water to about 1 molar sodium chloride, and a temperature in the range of from about 4° C. to about 45° C.; and may further include a time sufficient for binding to occur (e.g., in a range of from about 10 minutes to about 2 hours).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, and an amino acid precursor (e.g., citrulline and ornithine are intermediates in the synthesis of arginine). In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, and synthetic diaminocarboxylic acids such as 3,4-diaminobenzoic acid, 2,3-diaminopropionic acid, 2,4-diaminobutyric acid, 2,5-diaminopentanoic acid, and 2,6-diaminopimelic acid.

By the term "amino acid" is meant, for purposes of the specification and claims to refer to a molecule that has at least one free amine group and at least, one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary mono-aminocarboxylic acids include, but are not limited to, glycine, serine, threonine, cysteine, β-alanine, homoserine, γ-aminobutyric acid, homocysteine, and selenocysteine.

By the term "carboxylic acid" is meant, for purposes of the specification and claims to refer to a compound having the formula $HS(CH_2)_nX$, wherein X is a carboxylate (carboxylic moiety). "n" is a number in the range of from 1 to about 20, and preferably greater than 4. In a preferred embodiment, the thiol group of the carboxylic acid can be used as a reactive functionality for the carboxylic acid to become operably bound to the nanocrystal, depending on the composition of the nanocrystal (e.g., to Cd, Zn and the like). Additionally, the carboxylic moiety of the. carboxylic acid imparts water solubility to the nanocrystals. Exemplary carboxylic acids may include, but are not limited to, mercaptocarboxylic acid, or mercaptofunctionalized amines (e.g., aminoethanethiol-HCl, or 1-amino-2-methyl-2-propanethiol-HCl).

The following examples are illustrative of the methods and fluorescent microspheres of the present invention.

EXAMPLE 1

As disclosed in detail in U.S. application Ser. No. 09/372,729 (the disclosure which is herein incorporated by reference), fluorescent nanocrystals comprise nanocrystals which have been functionalized by the addition of a plurality of molecules; and preferably, the molecules are selected. from an amino acid, a carboxylic acid, and a combination thereof. For example, the nanocrystals may comprise semiconductor nanocrystals that have a core selected from the group consisting of CdSe, CdS, and CdTe (collectively referred to as "CdX"), and may further comprise a passivating shell comprised of YZ wherein Y is Cd or Zn, and Z is S, or Se. Typically, CdX core/YZ shell quantum dots are overcoated with trialkylphosphine oxide, with the alkyl groups most commonly used being butyl and octyl. In one preferred embodiment, the CdX core/YZ shell quantum dots are treated with a large excess of mercaptocarboxylic acid in exchanging the trialkylphosphine oxide coat with a coat comprising a plurality of carboxylic acid molecules. For example, (CdSe)ZnS nanocrystals were prepared in a pyridine solution. The pyridine overcoating of the (CdX) core/YZ shell nanocrystals were exchanged with a carboxylic acid comprising mercaptocarboxylic acid. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary to form a transparent solution. Chloroform was added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with molecules of carboxylic acid, were then soluble in water or other aqueous solutions. The nanocrystals, in an aqueous solution, were centrifuged once more, filtered through a 0.2 μm filter, degassed with argon, and stored in an amber vial. The nanocrystals may then be further functionalized by an amino acid comprising a diaminocarboxylic acid. The diaminocarboxylic acid molecules were operably bound to the carboxylic acid molecules of the nanocrystals by using commercially available crosslinking agents and methods known to those skilled in the art. For example, the carboxylic acid-coated nanocrystals were dissolved in an aqueous buffer system (pH of about 7). To the nanocrystals was added EDC (1-ethyl-3-[3-dimethylaminopropyl] carbodiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration and stirred for 15 minutes. The entire solution was then added drop-wise, with stirring, to a solution of a diaminocarboxylic acid comprising lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, fluorescent nanocrystals can be solubilized in an aqueous solution of choice. Once solubilized, the resulting solution can be stored in an amber vial under an inert gas to prevent flocculation. The fluorescent nanocrystals may be operably bound to a successive layer of amino acid molecules by, for example, repeating the procedure and reaction using EDC and sulfoNHS with the amino acid molecules comprising the successive layer.

Similarly, a nanocrystal comprising a doped metal oxide nanocrystal may be operably bound to a plurality of molecules (e.g., a carboxylic acid, and amino acid, or a combination thereof) using methods known in the art. For example, the plurality of molecules having reactive functionalities comprising free carboxyl groups can be chemisorbed, adsorbed or otherwise permanently added to the metal oxide portion of the nanocrystal. For example, the metal oxide nanocrystals are suspended in an aqueous solution of an amino acid comprising homocysteine having a pH of about 3.5 for about an hour. The reaction is then stopped by adjusting the pH to neutral, and dialyzing out the aqueous solution.

As an alternative, fluorescent nanocrystals functionalized with a plurality of homocysteine molecules were prepared as follows. Nanocrystals (e.g., (CdSe)ZnS) coated with an organic layer (e.g., mercaptoacetic acid) were treated with a molar excess of homocysteine in replacing the organic layer with a coating comprising a plurality of homocysteine molecules. The approximate number of surface Zn sites on the specific size of nanocrystals . utilized was calculated. At least a 5 times molar excess of homocysteine (as compared to the number of surface Zn sites) was added to the nanocrystals, as per the following formula. Grams homocysteine=5(number of Zn surface sites) (volume of solution containing the nanocrystals) (concentration of nanocrystals in solution) (135.2). The mixture was stirred to dissolve the homocysteine, and then stored at 4° C. for 24 hours. The resultant solution was then centrifuged to remove any precipitate, and the super-natant was transferred to a centrifugal filter for the appropriate volume of supernatant (preferably, with a molecular weight cutoff of about 10 kD or below to retain the fluorescent nanocrystals coated with homocysteine). After centrifugation, and when the desired minimum volume is reached, the fluorescent nanocrystals were then rediluted in the appropriate aqueous solution (e.g., HEPES buffer) to a volume in which the original mass of homocysteine had been dissolved. The steps of filtering and redilution of the fluorescent nanocrystals in solution may be repeated to improve purity. The resultant fluorescent nanocrystals comprising homocysteine-coated nanocrystals may then be degassed by bubbling with an inert gas, and then stored at 4° C. in an amber bottle.

EXAMPLE 2

This example illustrates embodiments of fluorescent microspheres, and a method of making the fluorescent microspheres, according to the present invention; wherein polymeric microspheres are contacted with fluorescent nanocrystals under suitable conditions for the fluorescent nanocrystals to become embedded into the polymeric microspheres in forming fluorescent microspheres. In a process of making these fluorescent microspheres, the polymeric microspheres are first exposed to conditions suitable for swelling them in size (e.g., also referred to as "expanded") so as to increase porosity in allowing fluorescent nanocrystals, present in the reaction process, to enter into pores at the surface of each swollen polymeric microsphere. The polymeric microspheres are then exposed to suitable conditions in which the polymeric microspheres become unswollen, thereby physically entrapping the fluorescent nanocrystals in the pores of the polymeric microspheres. Thus, by this process, the fluorescent nanocrystals become embedded in the surface of a polymeric microsphere.

In one embodiment of this example, the polymeric microspheres are swelled by exposing them to a temperature sufficient to soften the polymer composition of the polymeric microspheres, but below the melting point of the polymer composition. The suitable conditions may further comprise pressurizing the polymeric microspheres (e.g., to a pressure above atmospheric pressure) which can be used to shorten the time in which to heat the polymeric microspheres to make them swell. Suitable conditions for swelling polymeric microspheres to physically entrap fluorescent nanocrystals can be determined using methods customary in the art. As will be apparent to those skilled in the art, the time and temperature used to swell the polymeric microspheres will depend on the nature (e.g., composition) of the polymeric microspheres. For example, it is generally known that polymeric microspheres comprised of polystyrene can be softened at temperatures in the range of from about 200° C. to about 250° C. for a time of about 0.5 to about. 10 hours (depending on the type of polystyrene). Likewise, the amount of superatmospheric pressure to which the polymeric microspheres may be exposed will depend on the temperature of heating, and the nature (e.g., composition) of the polymeric microspheres. For example, to form fluorescent microspheres, the polymeric microspheres capable of being swelled to increase porosity are added to a solution containing the fluorescent nanocrystals, wherein the resultant reaction suspension is contained within a reaction vessel. The reaction suspension in the reaction vessel is then subjected to suitable conditions (e.g., heat, or heat and pressurization) to effect swelling of the polymeric microspheres and entry of the fluorescent nanocrystals into the pores of the swelled polymeric microspheres. The reaction is stopped (e.g., allow the suspension to cool to ambient temperature; or cooling with venting to reduce pressure to atmospheric) resulting in the unswelling of the polymeric microspheres, and the physical entrapment of fluorescent nanocrystals in forming fluorescent microspheres having a uniform distribution of fluorescent nanocrystals embedded therein. The process may further comprise purifying the fluorescent microspheres from any free fluorescent nanocrystals in the reaction suspension (e.g., by one or more of: size such as by centrifugation, size exclusion chromatography, and the like; by affinity chromatography if the fluorescent microspheres further comprise affinity ligand). It will be apparent to one skilled in the art that the ratio of fluorescent nanocrystals to polymeric microspheres may vary with factors which include, but are not limited to, the size of the polymeric microspheres, the desired fluorescent intensity of the resultant fluorescent microspheres, and the like. Preferably, the fluorescent nanocrystals are in a sufficient amount to saturate the surface of each polymeric microsphere present in the reaction. While not intended to be limiting, generally the amount of fluorescent nanocrystals in the reaction is less than or equal to about 20% by weight of the polymeric microspheres in the reaction.

In another embodiment, the polymeric microspheres are swelled by exposing them to an organic medium comprising one or more organic solvents which are able to swell the polymeric microspheres. The degree of swelling necessary for physically entrapping the fluorescent nanocrystals in the polymeric microspheres can be adjusted by the type and amount of solvent using customary methods. As will be apparent to those skilled in the art, the time of exposure to, and concentration of, the one or more solvents used to swell the polymeric microspheres will depend on the nature of the composition of the polymeric microspheres, and the composition of the organic medium used. For example, it is generally known that a wide variety of common liquid organic solvents can be used to swell polymeric microspheres in a controlled manner so as not to permanently damage the polymeric microspheres themselves. Useful solvents may include, but are not limited to, dimethyl sulfoxide (DMSO), dimethylformamide (DMF), toluene, tetrahydrofuran, chloroform, methylene chloride, acetones, acetonitrile, alcohols, or a combination thereof. In one preferred embodiment, the organic medium is water-miscible. In another preferred embodiment, the organic medium is in a concentration of 30% or more (v/v) for performing the swelling. For example, to form fluorescent microspheres, the polymeric microspheres capable of being swelled to increase porosity are added to organic medium comprising the one or more solvents, and also containing the fluorescent nanocrystals, wherein the resultant reaction suspension is contained within a reaction vessel for a sufficient time to effect the swelling of the polymeric microspheres. The reaction is stopped (e.g., by removing the organic medium from contacting the polymeric microspheres) resulting in unswelling of the polymeric microspheres, and the physical entrapment of fluorescent nanocrystals in forming fluorescent microspheres having a uniform distribution of fluorescent nanocrystals embedded therein. The process may further comprise purifying the fluorescent microspheres from any free fluorescent nanocrystals in the reaction suspension. (e.g., by one or more of: size such as by centrifugation, size exclusion chromatography, and the like; by affinity chromatography if the fluorescent microspheres further comprise affinity ligand). While not intending to be limiting, and in a preferred embodiment, generally the reaction is carried out at a temperature in the range of from about 5° C. to about 30° C. during a sufficient period of time for the organic medium to diffuse or absorb into the polymeric microspheres to cause their swelling. It will be apparent to one skilled in the art that the ratio of fluorescent nanocrystals to polymeric microspheres may vary with factors which include, but are not limited to, the size of the polymeric microspheres, the desired fluorescent intensity of the resultant fluorescent microspheres, and the like. Preferably, the fluorescent nanocrystals are in a sufficient amount to saturate the surface of each polymeric microsphere present in the reaction. While not intended to be limiting, generally the amount of fluorescent nanocrystals in-the reaction is less than or equal to about 20% by weight of the polymeric microspheres in the reaction.

In a preferred embodiment, the swellable polymeric microspheres (and the resultant fluorescent microspheres) further comprise multiple molecules of reactive functionality comprising a free chemical group which may include, but is not limited to, carboxyl, amine, amide, tiol, ester, sulfhydryl, and the like The surface reactive functionalities of a fluorescent microsphere may be used as a means for operably binding affinity ligand to the fluorescent microsphere, wherein the affinity ligand has a free chemical group which is reactive (in forming a bond) with the surface reactive functionalities of the microsphere. For example, using conventional chemistry, affinity ligand that may be operably bound to the surface of the fluorescent microspheres may include, but are not limited to, antibody, avidin, biotin, protein A or G, lectin, aptamer, a nucleic acid molecule (e.g., RNA, DNA, hybrids, single stranded, double stranded, synthetic, oligonucleotides, etc.), a carbohydrate chain, a protein with binding specificity for an analyte, and the like. The fluorescent microspheres that further comprise affinity ligand are then used as a detection reagent in an assay for determining the presence or absence of an analyte for which the affinity ligand has binding specificity, as is disclosed herein in more detail.

EXAMPLE 3

This example illustrates an embodiment of the fluorescent microspheres according to the present invention, as well as a process for making the fluorescent microspheres. The polymeric microspheres used in this illustration comprised amine-activated polystyrene-based beads of a size of about 7.3 $\mu$m. More particularly, their composition comprised 70% methylmethacrylate, 20% glycidylmethacrylate, and 10% ethylene glycol dimethacrylate. A 10% (w/w) suspension of the polymeric microspheres (in a volume of 10 $\mu$l) was diluted in a reaction vessel with an organic medium comprised of either of two solvents, DMSO or DMF (90 $\mu$l). To each was added 10 $\mu$l of a 10 $\mu$M fluorescent nanocrystal solution (in an aqueous buffer; e.g., HEPES), and the resultant reaction suspension was mixed and incubated at room temperature for a sufficient time for swelling of the polymeric microspheres. Although a sufficient time may comprise only minutes, in this case the reaction was allowed to proceed for a time that ranged from about 1 hour to about 24 hours. The reactions were stopped by adding to the respective reaction suspension a water-based buffer or water, and then removing the solvent. In this case, to each reaction suspension was added, and mixed with, 1 ml of HEPES buffer, followed by pelleting the resultant fluorescent microspheres by centrifugation (e.g., 2 minutes at 2000×g). Each preparation of fluorescent microspheres was washed again with the buffer, and then collected by centrifugation. Each of the preparations of fluorescent microspheres was then resuspended in 20 $\mu$l of buffer.

To confirm the formation of fluorescent microspheres, a 10 $\mu$l of each of the preparations of fluorescent microspheres was suspended in a non-aqueous medium (e.g., formalin solution (4% formaldehyde), dimethylsulfoxide, or mineral oil) and placed onto a microscopic slide for viewing under a fluorescence microscope. After excitation with ultraviolet light, and using a 425 nm long pass emission filter, each of the preparation of fluorescent microspheres was observed under fluorescent microscopy as being a strong red fluorescence (614 nm), characteristic of the fluorescent nanocrystals (homocysteine-coated (CdSe)ZnS) embedded in the fluorescent microspheres. To further illustrate an attendant advantage of the fluorescent microspheres according to the present invention, FIG. 1 illustrates the relative intensity of an exemplary fluorescent microspheres ("FM") compared to that of comparative fluorescent nanocrystals ("NC") used in producing the fluorescent microspheres, expressed as a ratio of FM:NC, and with respect to concentration of analyte ("antigen"). As previously described herein, in a detection assay the intensity of the fluorescent microspheres having affinity ligand bound thereto significantly increases, compared to comparative functionalized nanocrystals having affinity ligand bound thereto, as the concentration of analyte (for which the affinity ligand has binding specificity) decreases.

EXAMPLE 4

This example illustrates another embodiment of fluorescent microspheres, and a method of making the fluorescent microspheres, according to the present invention; wherein polymeric microspheres are swelled and unswelled under suitable conditions so as to physically entrap fluorescent nanocrystals in forming fluorescent microspheres, and wherein the fluorescent midrospheres further comprise a plurality of molecules of affinity ligand which are contacted with the fluorescent microspheres under suitable conditions for affinity ligand to be operably bound to the fluorescent microspheres. In one preferred embodiment of the present invention, the fluorescent microspheres are formed first, and then affinity ligand is operaly bound thereto in producing fluorescent microspheres further comprising affinity ligand according to the present invention. In illustrating this preferred embodiment, fluorescent microspheres are made according to the methods described in Example 2 or Example 3 herein. To approximately $1.4 \times 10^7$ fluorescent microspheres (in a volume of 500 $\mu$l aqueous solution) is added 2 mg of EDC (in 100 $\mu$l aqueous solution) and 5 mg sulfo-NHS (in 100 $\mu$l aqueous solution), and the mixture is mixed for 10 minutes. Mercaptoethanol (1 $\mu$l) is added to the mixture with stirring for 5 minutes. Affinity ligand (in this illustrative embodiment, neutravidin; long) is added to the mixture with stirring for 1 hour. TRIS (30 mM) is then added to the mixture with stirring for 30 minutes. The resultant fluorescent microspheres are then pelleted by centrifugation, washed several times in aqueous solution to wash away free neutravidin, and then resuspended in an aqueous solution.

EXAMPLE 5

This example illustrates another embodiment of fluorescent microspheres according to the present invention, and further illustrates a method of making the fluorescent microspheres according to the present invention. In this illustrative embodiment the fluorescent microspheres comprised fluorescent nanocrystals operably bound to polymeric microspheres comprising a magnetic responsive material ("magnetic material") with a polymeric, nonmagnetic coating. Such polymeric microspheres are known to include general characteristics as follows. First, magnetic materials useful for the microspheres may include, but are not limited to, ferromagnetic, ferrimagnetic, paramagnetic, superparamagnetic materials, and the like. Such magnetic materials may include, but are not limited to: metals, such as nickel, iron, cobalt, chromium, manganese, and the like; lanthanide series elements, such as neodymium, erbium, and the like; alloys such as magnetic alloys of metals; metal oxides, such as ferric oxide, chromium oxide, nickel oxide, and the like; composites, such as ferrites, magnetite, and the like; and combinations thereof. As will be appreciated by those, skilled in the art, the diameter of a core of magnetic material core may vary widely depending on the size of the polymeric microsphere of which it is a part; the composition, shape, size and density of the magnetic material; and the assay protocol in which the polymeric microsphere is used. In a preferred embodiment, the diameter of a magnetic material core is a size in the range of from about 0.01 $\mu$m to about 10 $\mu$m. Polymeric materials which may be used to coat a magnetic material core, have been previously described herein in more detail. As known to those skilled in the art, the polymeric microspheres comprising magnetic material may comprise: a magnetic material core and a polymeric, nonmagnetic coating; a nonmagnetic core (e.g., polymeric or other nonmagnetic material) with a magnetic material layer thereon, and a polymeric, nonmagnetic coating; and a magnetic material dispersed within a polymeric, nonmagnetic material (such as may be obtained by mixing the magnetic material into a solution of a thermoplastic, and then plasticizing the mixture into a solid composite). For example, commercially-obtained polymeric microspheres comprising polymer-coated magnetite may be used in the process according to Example 2 or Example 3 herein, in physically entrapping fluorescent nanocrystals in forming fluorescent microspheres. The resultant fluorescent microspheres may further comprise affinity ligand by using a process according to Example 4 herein.

EXAMPLE 6

This example illustrates one embodiment of a method of using the fluorescent microspheres according to the present invention to provide an identifiable fluorescence signal pattern. For example, semiconductor nanocrystals can be produced in several uniform sizes, with each size comprising a homogeneous population capable of emitting a discrete fluorescence emission of high quantum yield (i.e., the particular color emitted is primarily dependent on the size of the nanocrystal), but wherein the heterogeneous population (a combination of homogeneous populations) can be excited with a single wavelength spectrum of light, and can emit a distinguishably detectable ("discrete") fluorescence emission spectra representative of the homogenous populations. Likewise, depending on the dopant for a doped metal oxide nanocrystal, a homogeneous population (e.g., containing the same type and amount of dopant) is capable of emitting a discrete fluorescence emission-of high quantum yield, but wherein the heterogeneous population (a combination of homogeneous populations) can be excited with a single wavelength spectrum of light, and can emit a distinguishably detectable fluorescence emission spectra representative of the homogenous populations. Thus, a fluorescent microsphere may comprise an identifiable fluorescence signal pattern comprised of one (e.g., capable of fluorescing a single color) or more (capable of fluorescing in multicolor) homogeneous populations of fluorescent nanocrystals which comprise a part (component) of the fluorescent microsphere. For example, where the fluorescent microsphere comprises a homogeneous population of fluorescent nanocrystals, the fluorescent nanocrystals may be dispersed by physical entrapment to cover the general shape of the fluorescent microsphere in providing a fluorescence signal pattern comprised of a single color of fluorescence, and as measured by a peak intensity. Likewise, where the fluorescent microsphere comprises a heterogeneous population of fluorescent nanocrystals, the fluorescent nanocrystals may be dispersed by physical entrapment to cover the general shape of the fluorescent microsphere in providing a fluorescence signal pattern comprised of more than one color of (multicolor) fluorescence with each color capable of being detectably distinguishable from the other color or colors by their peak emission spectra (e.g., are spectrally resolvable). Also, a fluorescence signal pattern emitted by a fluorescent microsphere may comprise a multicolor fluorescence, and may comprise detectably distinguishable intensities of one or more colors. A code representative of the fluorescence signal pattern, and of the fluorescent microsphere which emits the fluorescence signal pattern, may comprise an identifier (e.g., one or more numbers) assigned for each color comprising the fluorescence signal pattern, and may further comprise an identifier representative of the intensity of each color comprising the fluorescence signal pattern (e.g., wherein the code comprises a combination of the identifiers, such as a string of numbers in a range of from about 2 numbers to about 100 numbers). Thus, an identifiable fluorescence signal pattern comprised of a plurality of colors (or colors and intensities) enables a large number of combinations and permutations which may be used to identify or track a fluorescent microsphere by exposing the fluorescent microsphere to an exciting light source and detecting the resultant fluorescence emission. Thus, fluorescent microspheres may be used in multidimensional array formats (e.g., microarrays) for detecting a plurality of analytes by depositing on and/or flowing the fluorescent microspheres in the desired array format, and utilizing an appropriate detection system to detectably distinguish the fluorescent signal patterns (e.g., as measured by number of events of fluorescence versus the intensity of fluorescence, using a fluorescence microscope with a video camera attachment and computer software program for manipulating and storing the data collected).

EXAMPLE 7

This example illustrates another embodiment of a method of using the fluorescent microspheres according to the present invention for determining the presence or absence of a predetermined number of analytes in a sample. The determination may be qualitative or quantitative, depending on the assay format utilized. A predetermined number of analytes means a single analyte if it is desired to determine the presence or absence of that analyte alone; or more than one analyte when it is desired to determine the presence or absence of any one or more of multiple analytes. The fluorescent microspheres may comprise a homogenous population which is capable of fluorescing a peak emission (fluorescent signal pattern) when excited by an excitation light source, and further comprises affinity ligand having binding specificity for the analyte of which the presence or absence is to be determined. Alternatively, the fluorescent microspheres may comprise a heterogeneous population comprising multiple homogenous populations, wherein each homogenous population is capable of emitting a fluorescence signal pattern distinguishable (e.g., spectrally) from the fluorescence signal patterns of other homogenous populations comprising the heterogeneous population, and wherein the heterogeneous population may be excited by a single excitation light source. Each homogenous population of the heterogeneous population may further comprise affinity ligand having binding specificity for an analyte of the predetermined number of analytes of which the presence or absence is to be determined. Thus, a method of using the fluorescent microspheres for determining the presence or absence of a predetermined number of analytes in a sample comprises:

(a) contacting the fluorescent microspheres with the sample under suitable conditions for affinity ligand of the fluorescent-microspheres to bind the predetermined number of analytes, if present in the sample, in forming complexes;

(b) exposing the complexes, if formed, to an excitation wavelength light source suitable for exciting the fluorescent microsphere's of the complexes to emit a fluorescence signal pattern; and (c) detecting the fluorescence signal pattern emitted by the complexes, if present, by a detection means for detecting the fluorescence signal pattern;

wherein detection of the fluorescent signal pattern is indicative of the presence of an analyte of the predetermined number of analytes. Wherein the presence of an analyte is detected, the method may further comprise quantitating the amount of analyte by measuring the intensity of the fluorescence signal pattern emitted from the fluorescent microspheres bound to the analyte, and relating the intensity measured to the amount of analyte. The method may be used in a fluorescent detection system selected from the group consisting of an affinity-based assay, fluorescence-based immunoassay, fluorescent staining (e.g., immunofluorescent staining on a glass slide), flow cytometry, a hybridization-based assay, screening of a library of sequences (protein or peptide or nucleic acid molecule) for a desired sequence ("combinatorial analysis"), and the like.

In a preferred embodiment, the fluorescence signal pattern comprises one or more fluorescence emission peaks, wherein each peak has a narrow spectral band (e.g. between about 4 nm to about 50 nm) in the range of from about 400 nm to about 800 nm. A preferred excitation light source for exciting the fluorescent microspheres according to the present invention is in the range of about 300 nm to about 400 nm; and in a more preferred embodiment, from about 360 nm to about 365 nm; and in a further preferred embodiment, with blue light (e.g., mid 400s to 486 nm). Any fluorescence signal pattern emitted is then detected and imaged by appropriate detection means or system (e.g., one or more of: photodetector, filter, charge couple device camera (CCD camera) fluorimeter, fluorescence microscope, a fluorescence cube, a computer for manipulating fluorescence signal pattern data collected, and a combination thereof).

EXAMPLE 8

In this example, illustrated is an embodiment of a kit which comprises one or a combination of types of fluorescent microspheres according to the present invention. For example, a kit may be provided which comprises one or more separate containers, wherein each container has contents comprising fluorescent microspheres capable of fluorescing a specific fluorescence pattern (e.g., one color or a desired combination of colors). In one example, the fluorescent microspheres may comprise reactive functionalities which allow a user of the kit to operably bind affinity ligand of the user's choice to the fluorescent microspheres. Thus, the kit may provide the user with the flexibility to prepare a customized detection reagent comprising the fluorescent microspheres operably bound to affinity ligand of the user's choice. In further illustration, the kit may comprise 3 containers, wherein one container has contents comprising fluorescent microspheres capable of fluorescing red; a second container has contents comprising fluorescent microspheres capable of fluorescing yellow; a third container has contents comprising fluorescent microspheres capable of fluorescing green; wherein the contents of each container are capable of being operably bound to affinity ligand via the reactive functionalities of the respective type (e.g., fluorescing color) of fluorescent microspheres. Alternatively, the different types (e.g., the three types distinguished above by color of fluorescence/specific fluorescence pattern) may all be contents of a single container.

In another example, the fluorescent microspheres: contained in each separate container comprising the kit further comprise affinity ligand operably bound thereto. Thus, the fluorescent microspheres may be used as detection reagents as described herein in more detail. For example, the kit may comprise a single container having contents comprising fluorescent microspheres further comprising affinity ligand having binding specificity for a desired analyte; or may comprise more than one type of fluorescent microspheres wherein each individual type has affinity ligand having a different binding specificity than affinity ligand of the other types of fluorescent microspheres in the single container. Alternatively, each of plurality of types of fluorescent microspheres (differing in binding specificity) may be individually packaged in a separate container, such that the kit is now comprised of a plurality of containers.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A fluorescent microsphere comprised of a plurality of fluorescent nanocrystals physically entrapped in a polymeric microsphere, wherein the fluorescent nanocrystals are functionalized with a plurality of molecules selected from the group consisting of carboxylic acid, diaminocarboxylic acid, monoaminocarboxylic acid, and a combination thereof.

2. The fluorescent microsphere according to claim 1, wherein the polymeric microsphere comprises multiple molecules of reactive functionality comprising a free chemical group.

3. The fluorescent microsphere according to claim 1, wherein physically entrapped in the polymeric microsphere is a homogenous population of fluorescent nanocrystals.

4. The fluorescent microsphere according to claim 1, wherein physically entrapped in the polymeric microsphere is a heterogeneous population of fluorescent nanocrystals.

5. The fluorescent microsphere according to claim 2, further comprising affinity ligand operably bound thereto.

6. The fluorescent microsphere according to claim 1, wherein the fluorescent nanocrystals have an average particle size of approximately 1 nm to approximately 20 nm.

7. The fluorescent microsphere according to claim 1, wherein the fluorescent nanocrystals comprise semiconductor nanocrystals.

8. The fluorescent microsphere according to claim 7, wherein the fluorescent nanocrystals have a particle size that varies by less than 4%.

9. The fluorescent microsphere according to claim 1, wherein the fluorescent nanocrystals comprise doped metal oxide nanocrystals.

10. The fluorescent microsphere according to claim 9, wherein the fluorescent microsphere is magnetic.

11. The fluorescent microsphere according to claim 1, wherein the polymeric micro6sphere further comprises carbon black in a weight percentage of from about 0.5 to about 5.

12. The fluorescent microsphere according to claim 1, wherein the polymeric microsphere comprises a combination of a polymeric material and a magnetic material selected from the group consisting of a polymeric material into which is embedded the magnetic material, a magnetic material core and a polymeric material coating, a polymeric material coating over the magnetic layer, and a magnetic material dispersed within a polymeric material.

13. The fluorescent microsphere according to claim 3, wherein the homogenous population of fluorescent nanocrystals, when excited with an excitation light source, emit a fluorescence signal pattern observable as a single color.

14. The fluorescent microsphere according to claim 4, wherein the heterogeneous population of fluorescent nanocrystals, when excited with an excitation light source, emit a fluorescence signal pattern observable as more than one color.

15. The fluorescent microsphere according to claim 14, wherein the fluorescence signal pattern comprises multicolor fluorescence and detectably distinguishable intensities.

16. The fluorescent microsphere according to claim 15, wherein a code representative of the fluorescence signal pattern, and of the fluorescent microsphere which emits the fluorescence signal pattern, comprises an identifier for each color comprising the fluorescence signal pattern, and an identifier for the intensity of each color.

17. The fluorescent microsphere according to claim 16, wherein the code comprises a string of numbers.

18. The fluorescent microsphere according to claim 1,
wherein the fluorescent nanocrystals comprise a homogeneous population of semiconductor nanocrystals functionalized with a plurality of molecules comprised of carboxylic acid; and wherein said polymeric microsphere includes a magnetic material embedded into a polymeric material.

19. A fluorescent microsphere comprising:

a fluorescent nanocrystal; and a polymeric microsphere physically entrapping the fluorescent nanocrystal.

20. The fluorescent microsphere as set forth in claim 19, the fluorescent nanocrystal being functionalized with a plurality of molecules selected from the group consisting of carboxylic acid, diaminocarboxylic acid, monoaminocarboxylic acid, and a combination thereof.

21. The fluorescent microsphere as set forth in claim 19, where the polymeric microsphere physically entraps a homogenous plurality of fluorescent nanocrystals.

22. The fluorescent microsphere as set forth in claim 21, where the homogenous plurality of fluorescent nanocrystals selectively emit a single color.

23. The fluorescent microsphere as set forth in claim 19, where the polymeric microsphere physically entraps a heterogeneous plurality of fluorescent nanocrystals.

24. The fluorescent microsphere as set forth in claim 23, where the heterogeneous plurality of fluorescent nanocrystals selectively emit a plurality of colors.

25. The fluorescent microsphere of claim 24, where ones of the plurality of colors comprise a distinguishable intensity from another of the plurality of colors.

26. The fluorescent microsphere of claim 19, where the fluorescent nanocrystal comprises a semiconductor nanocrystal.

27. The fluorescent microsphere of claim 19, where the fluorescent nanocrystal comprises a doped metal oxide nanocrystal.

28. The fluorescent microsphere of claim 19, where the fluorescent microsphere is magnetic.

29. The fluorescent microsphere of claim 19, where the polymeric microsphere further comprises carbon black in a weight percentage of from about 0.5 to about 5.

30. The fluorescent microsphere of claim 19, the polymeric microsphere comprising a combination of a polymeric material and a magnetic material.

31. A luminescent tagging agent comprising:
at least one fluorescent nanocrystal; and
a polymeric microsphere at least partially entrapping the fluorescent nanocrystal.

32. The luminescent tagging agent as set forth in claim 31, where the fluorescent nanocrystal is functionalized with a plurality of molecules selected from the group consisting of carboxylic acid, diaminocarboxylic acid, monoaminocarboxylic acid, and a combination thereof.

33. The luminescent tagging agent as set forth in claim 31, where the polymeric microsphere comprises multiple molecules of reactive functionality comprising a free chemical group.

34. The luminescent tagging agent as set forth in claim 31 further comprising a plurality of fluorescent nanocrystals that selectively fluoresce at substantially similar wavelengths.

35. The luminescent tagging agent as set forth in claim 31 further comprising at least two fluorescent nanocrystals that selectively fluoresce at detectably different wavelengths.

36. The luminescent tagging agent as set forth in claim 31 further comprising an affinity ligand operably bound thereto.

37. The luminescent tagging agent as set forth in claim 31, where the polymeric microsphere comprises a diameter in the range of 0.05 $\mu$m to 500 $\mu$m.

38. The luminescent tagging agent as set forth in claim 31, where the polymeric microsphere is magnetic.

39. The luminescent tagging agent as set forth in claim 34, where the fluorescent nanocrystaly selectively fluoresce at detectably distinguishable intensities.

40. The luminescent tagging agent as set forth in claim 31 further comprising an analyte operably bound to the luminescent tagging agent.

* * * * *